United States Patent
Geiger

(10) Patent No.: US 11,452,481 B2
(45) Date of Patent: Sep. 27, 2022

(54) SYSTEM AND METHOD OF TESTING FOR LEAKS AFTER ANASTOMOSIS

(71) Applicant: Vanderbilt University, Nashville, TN (US)

(72) Inventor: Timothy M. Geiger, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 667 days.

(21) Appl. No.: 16/096,599

(22) PCT Filed: Apr. 27, 2017

(86) PCT No.: PCT/US2017/029931
§ 371 (c)(1),
(2) Date: Oct. 25, 2018

(87) PCT Pub. No.: WO2017/189900
PCT Pub. Date: Nov. 2, 2017

(65) Prior Publication Data
US 2020/0297274 A1    Sep. 24, 2020

Related U.S. Application Data

(60) Provisional application No. 62/328,346, filed on Apr. 27, 2016.

(51) Int. Cl.
*A61B 5/00*    (2006.01)
*A61K 9/12*    (2006.01)
(Continued)

(52) U.S. Cl.
CPC .......... *A61B 5/4848* (2013.01); *A61B 5/4255* (2013.01); *A61K 9/122* (2013.01);
(Continued)

(58) Field of Classification Search
CPC .... A61B 5/4848; A61B 5/4255; A61K 9/122; A61K 49/0002; A61M 5/19; A61M 39/105

See application file for complete search history.

(56) References Cited

U.S. PATENT DOCUMENTS 4,197,316 A  *  4/1980  Yu .......................... A61K 8/365
                                                        514/459
8,216,159 B1     7/2012  Leiboff
(Continued)

FOREIGN PATENT DOCUMENTS

WO    2008051925 A2    5/2008
WO    2016022816 A1    2/2016
WO    2016022973       2/2016

OTHER PUBLICATIONS

"What's New, CO2? Get to Know a Chemical Reaction," Teacher's Guide (Year: 2009).*
(Continued)

*Primary Examiner* — Daniel L Cerioni
(74) *Attorney, Agent, or Firm* — Michael Best & Friedrich LLP

(57) ABSTRACT

Devices, kits, and methods for testing the integrity of a cavity within an anatomical organ. For example, the devices, kits, and methods described herein are useful for detecting leaks in an anastomosis or for testing the integrity or repair of a defect in anatomy.

14 Claims, 3 Drawing Sheets

(51) Int. Cl.
  *A61K 49/00* (2006.01)
  *A61M 5/19* (2006.01)
  *A61M 39/10* (2006.01)
  *A61B 17/11* (2006.01)

(52) U.S. Cl.
  CPC .......... *A61K 49/0002* (2013.01); *A61M 5/19* (2013.01); *A61M 39/105* (2013.01); *A61B 17/1114* (2013.01)

(56) References Cited

U.S. PATENT DOCUMENTS

| | | | |
|---|---|---|---|
| 2004/0018228 A1* | 1/2004 | Fischell | A61K 9/127 |
| | | | 424/450 |
| 2006/0216256 A1 | 9/2006 | Giniger et al. | |
| 2006/0217637 A1* | 9/2006 | Leiboff | A61M 31/00 |
| | | | 600/593 |
| 2008/0004566 A1 | 1/2008 | Sloan | |
| 2008/0275403 A1 | 11/2008 | Maaskamp et al. | |
| 2008/0312559 A1 | 12/2008 | Santilli et al. | |
| 2013/0138132 A1* | 5/2013 | Phee | A61M 25/10181 |
| | | | 606/192 |
| 2014/0081169 A1* | 3/2014 | Gerding | A61B 1/015 |
| | | | 600/560 |
| 2014/0221732 A1* | 8/2014 | Dayton | A61B 17/70 |
| | | | 600/30 |
| 2015/0017682 A1 | 1/2015 | Adam | |
| 2015/0018597 A1* | 1/2015 | Fierens | A61M 5/142 |
| | | | 600/4 |
| 2015/0045725 A1 | 2/2015 | Smith et al. | |
| 2015/0351730 A1 | 12/2015 | Stokes et al. | |
| 2018/0221633 A1* | 8/2018 | Brister | A61F 5/0089 |

OTHER PUBLICATIONS

Japanese Patent Office Action for Application No. 2018-555891 dated Mar. 4, 2021 (5 pages including English translation).
Australian Patent Office Examination Report No. 1 for Application No. 2017258311 dated May 3, 2021 (3 pages).
PCT/US2017/029931 International Search Report and Written Opinion of the International Searching Authority dated Jul. 21, 2017 (13 pages).
European Patent Office Extended Search Report for Application No. 17790463.8 dated Dec. 2, 2019 (10 pages).
European Patent Office Examination Report for Application No. 17790463.8 dated Nov. 3, 2021 (6 pages).

* cited by examiner

SYSTEM AND METHOD OF TESTING FOR LEAKS AFTER ANASTOMOSIS

CROSS-REFERENCE TO RELATED APPLICATIONS

This application is a national stage filing under 35 U.S.C. § 371 of International Patent Application No. PCT/US2017/029931, which claims priority to U.S. Provisional Patent Application No. 62/328,346, filed Apr. 27, 2016, the contents of which are herein incorporated by reference.

BACKGROUND OF THE INVENTION

The creation of a bowel anastomosis (either stapled or hand sewn) is not a new concept in surgery and is common in general surgery, urology, gynecology, and surgical oncology procedures. Leaks from anastomosis are one of the most devastating problems for abdominal surgery. Morbidity and 30 day mortality associated with anastomotic leaks are 98% and 8.4% respectively. Length of stay is increased over 2.5× as compared to patients that do not experience a leak. In addition to increasing length of stay, costs are significantly higher for patients with leaks than those without.

For anastomosis of the left colon or rectum, there is a reliable method to check to make sure the connection is airtight (leak test). Currently, there is no effective way to test an anastomosis of the small bowel or the right side of the colon.

SUMMARY OF THE INVENTION

Embodiments of the invention provide a device, a kit, and a method for detecting leaks in an anastomosis or for testing the integrity of repair of a defect in anatomy. The embodiments described herein can be applied to the gastrointestinal tract (e.g., stomach, small intestine, large intestine, colon, rectum, etc.), urinary tract (e.g., bladder), or vagina. The device can be used to test the integrity of any connection or repair of the GI tract, or test the integrity or repair of the bladder or vagina.

In one embodiment, the invention provides a delivery device for detecting leaks in an anastomosis. The device comprises a first syringe and a second syringe. The first syringe comprises a base, and includes a first body, a first plunger, and a first outlet. The second syringe comprises an acid, and includes a second body, a second plunger, and a second outlet. The device also includes tubing having a first channel coupled to the first outlet, a second channel coupled to the second outlet, and a third channel configured to be received in a lumen of a cavity such that the acid and the base combine in the cavity where a gas is produced in the cavity and escapes through a defect of an anastomosis of the cavity/lumen showing any defect in the repair or connection.

In another embodiment, the invention provides a delivery device for testing integrity or repair of a defect in anatomy. The device comprises a first syringe and a second syringe. The first syringe comprises a base, the first syringe including a first body, a first plunger, and a first outlet. The second syringe comprises an acid, the second syringe including a second body, a second plunger, and a second outlet. The device also includes a delivery tube extending from the first outlet and the second outlet to deliver the acid and base to a cavity in the anatomy where a gas is produced in the cavity and escapes through a defect, if present, in the anatomy.

In a further embodiment, the invention provides a kit for testing for leaks of an anastomosis. The kit comprises a first syringe including a first body, a first plunger, and a first outlet and a second syringe including a second body, a second plunger, and a second outlet. The kit also comprises a first container comprising a base and a second container comprising an acid. The kit further comprises Y-tubing including a first channel connectable to the first outlet, a second channel connectable to the second outlet, and a third channel configured to be received in a lumen of a cavity such that the acid and the base combine in the cavity where a gas is produced in the cavity and escapes through a defect of an anastomosis of the cavity.

In yet another embodiment, the invention provides a method for testing for leaks of an anastomosis. The method comprises inserting an outlet of a delivery device into a lumen of an anastomosis of a bowel, delivering a sufficient amount of an acid and a sufficient amount of a base to the bowel, producing a gaseous foam when the acid and base enter the bowel to distend the bowel, showing any area needing repair if the gaseous foam exits through defects in the anastomosis, and retracting the outlet of the delivery device from the lumen of the anastomosis.

In another embodiment, the invention provides a delivery device for testing the integrity of a cavity within an anatomical organ. The device comprises a first syringe comprising a base, the first syringe including a first body, a first plunger, and a first outlet and a second syringe comprising an acid, the second syringe including a second body, a second plunger, and a second outlet. The device further comprises a delivery tube comprising a first channel extending from the first outlet and a second channel extending from the second outlet, the delivery tube having a distal end being configured to deliver the acid and the base to a cavity within an anatomical organ wherein the acid and base combine to produce a gaseous foam, and wherein the gaseous foam escapes through a defect, if present, in the anatomical organ.

In yet another embodiment, the invention provides a kit for testing the integrity of a cavity within an anatomical organ. The kit comprises a first syringe including a first body, a first plunger, and a first outlet, a second syringe including a second body, a second plunger, and a second outlet, a first container comprising a base, a second container comprising an acid, and Y-tubing including a first channel connectable to the first outlet and a second channel connectable to the second outlet, and a distal end configured to be received in a cavity within an anatomical organ such that the acid and the base combine within the cavity such that a gaseous foam is produced in the cavity and escapes through a defect, if present, in the anatomical organ.

In a further embodiment, the invention provides a method for testing the integrity of a cavity within an anatomical organ. The method comprises delivering a sufficient amount of an acid and a sufficient amount of a base into the cavity, thereby forming a mixture of an acid and a base within the cavity, and thereby producing a gaseous foam within the cavity and identifying any defects through which the gaseous foam exits the cavity.

DETAILED DESCRIPTION

Figure 1:
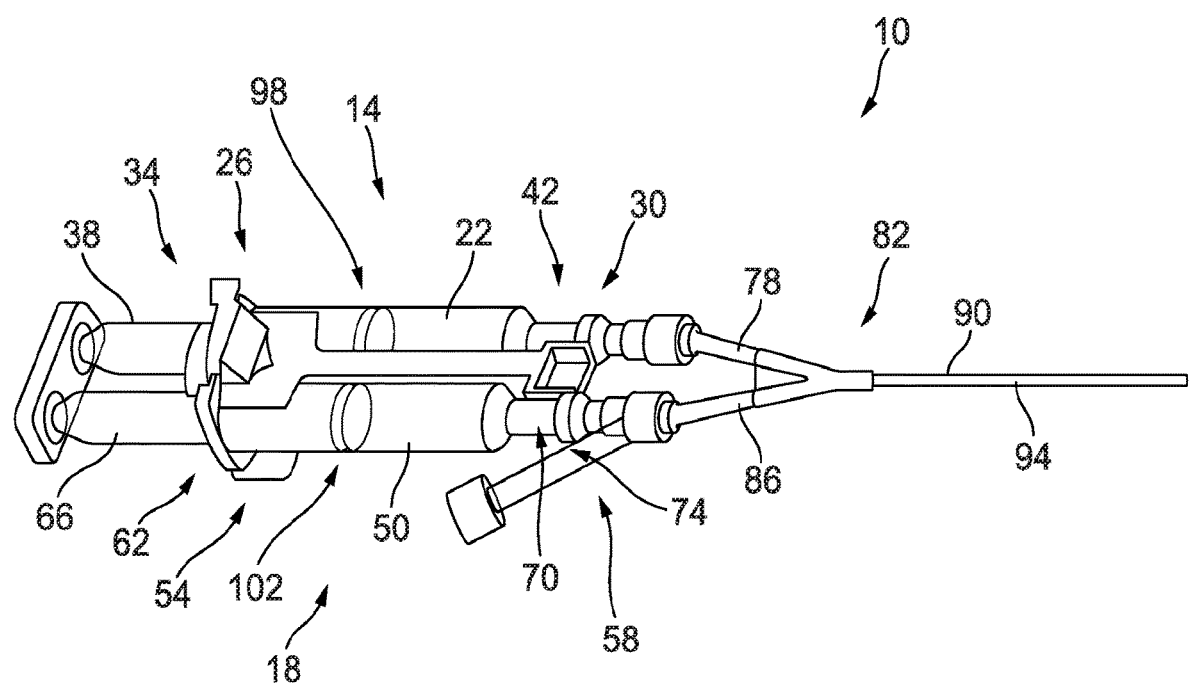
FIG. 1 illustrates a delivery device for detecting leaks in an anastomosis according to an embodiment of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Provided herein are devices, kits, and methods for testing the integrity of a cavity within an anatomical organ. For example, the devices, kits, and methods described herein are useful for detecting leaks in an anastomosis or for testing the integrity or repair of a defect in anatomy. The devices, kits, and methods described herein can be used to detect leaks or test the integrity or repair of any cavity, interior space, or lumen within any anatomical organ, including but not limited to those of the gastrointestinal tract (e.g., stomach, small intestine, large intestine, colon, rectum, etc.), urinary tract (e.g., bladder), or vagina. For example, the devices, kits, and methods described herein can be used to test the integrity of any connection or repair of the GI tract, or to test the integrity or repair of the bladder or vagina.

For example, some embodiments of the present invention provide a method of identifying technical defects that remain in an anastomosis no matter where the location of the connection is (e.g., small bowel, right colon, left colon, or rectum). It is known that identification of leaks at the time of creating the anastomosis allows for repair of the leak and dramatically reduces the clinical leak rate in the postoperative period.

Some embodiments of the present invention decrease the risk of a leak by identification of defects in the anastomosis that cannot be seen. These and other embodiments may provide a simple, fast acting, reliable method of leak detection.

As used herein, the term "cavity" refers to any cavity, lumen, or other interior space within an anatomical organ.

Methods

Provided herein are methods for testing the integrity of a cavity within an anatomical organ.

For example, the method can comprise delivering a sufficient amount of an acid and a sufficient amount of a base into the cavity, thereby forming a mixture of an acid and a base within the cavity, and thereby producing a gaseous foam within the cavity. The method can further comprise identifying any defects through which the gaseous foam exits the anatomical organ.

In some instances, it may be desirable to deliver the acid and base to the cavity simultaneously. Alternatively, the acid and the base may be delivered to the cavity sequentially, in either order.

The acid and the base may be delivered into the cavity using any means known in the art. For example, the method may comprise delivering the acid into the cavity using a first delivery device and delivering the base into the cavity using a second delivery device. More preferably, both the acid and the base are delivered into the cavity using a delivery device as described herein.

The methods described herein can be used to detect leaks or test the integrity or repair of any cavity, interior space, or lumen within any anatomical organ, including but not limited to those of the gastrointestinal tract (e.g., stomach, small intestine, large intestine, colon, rectum, etc.), urinary tract (e.g., bladder), or vagina.

For example, the methods described herein may be used to test the integrity of an organ of the gastrointestinal tract, including but not limited to the stomach, small intestine, large intestine, colon, and rectum. The methods described herein may be particularly useful for testing the integrity of a bowel, and in particular the integrity of an anastomosis of a bowel.

The acid and the base may be selected as described above, and are preferably delivered to the cavity in a molar ratio as described above.

The methods can further comprise delivering a colorant to the cavity. Among other advantages, the presence of a colorant facilitates the easy identification of the gaseous foam produced by the mixture of the acid and base, for example by producing a colored gaseous foam. This in turn facilitates the easy identification of any defects in the anatomical organ, which will be indicated by the presence of a colored gaseous foam escaping through such a defect. The colorant may be selected as described above.

The methods may further comprise repairing a defect in the anatomical organ, if necessary. For example, where the method is used to test for leaks in an anastomosis, the method may further comprise repairing the anastomosis if a defect is identified wherein the gaseous foam exits the anastomosis.

Kits

Also provided herein is a kit for testing the integrity of a cavity within an anatomical organ. Generally, the kit comprises a first syringe including a first body, a first plunger, and a first outlet; a second syringe including a second body, a second plunger, and a second outlet; a first container comprising a base; and a second container comprising an acid.

The acid and the base may be selected as described above, and the kit preferably comprises the acid and the base in a molar ratio as described above.

The kit can further comprise tubing configured to deliver the acid and the base to a cavity within an anatomical organ. For example, the kit may comprise Y-tubing including a first channel connectable to the first outlet and a second channel connectable to the second outlet, and a distal end configured to be received in a cavity within an anatomical organ.

In some embodiments, the kit tubing that includes a mixing area wherein the acid and the base are combined. For example, the kit may comprise Y-tubing including a first channel connectable to the first outlet, a second channel connectable to the second outlet, an area for mixing, and a third channel connected to the mixing area and configured to be received in a cavity configured to be received in a cavity within an anatomical organ, such that the acid and the base combine in the mixing area to form a mixture that travels through the third channel and into the cavity.

The kit may comprise a coupler configured to connect the first plunger to the second plunger, such that the first plunger and the second plunger can be depressed simultaneously.

The kit may further comprise a colorant, which may be selected as described above. A colorant may be incorporated into the first container, the second container, or both. Alternatively, the kit may comprise a third container comprising a colorant.

Delivery Devices

Also provided herein is a device configured to deliver an acid and a base to a cavity within an anatomical organ. The acid and the base combine to produce a gas, which escapes through any defects present in the anatomical organ, and thus enables such defects to be readily identified.

In preferred embodiments, the delivery device comprises a first syringe comprising a base, and including a first body, a first plunger, and a first outlet; and a second syringe comprising an acid, and including a second body, a second plunger, and a second outlet.

Typically, the delivery device further comprises tubing configured to deliver the acid and the base to a cavity within an anatomical organ.

The delivery device can comprise a delivery tube comprising a first channel extending from the first outlet and a second channel extending from the second outlet, wherein the distal end of the delivery tube is configured to deliver the acid and the base to a cavity within an anatomical organ. For example, the delivery tube can be configured such that the base exits the distal end of the tube through the first channel and the acid exits the distal end of the tube through the second channel.

In some embodiments, the distal end of the delivery tube that is configured to deliver the acid and the base to a cavity within an anatomical organ may comprise a needle.

The delivery device may comprise a mixing area wherein the acid and the base are combined prior to being delivered into the anatomical organ. For example, the delivery device can comprise a mixing chamber configured to receive the base from a first outlet and the acid from a second outlet, and combine the base with the acid to form a mixture. The device may further comprise a delivery tube extending from the mixing chamber and configured to deliver the mixture to a cavity within an anatomical organ.

The mixing area may be incorporated into the delivery tube. For example, the delivery device may comprise tubing having a first channel coupled to a first outlet, a second channel coupled to a second outlet, an area for mixing, and a third channel connected to the mixing area and configured to be received in a cavity within an anatomical organ.

In some instances, it may be desirable to deliver the acid and base to the cavity simultaneously. Accordingly, the delivery device may comprise a coupler that connects a first plunger of a first syringe to a second plunger of a second syringe, such that the first plunger and the second plunger can be depressed simultaneously. Alternatively, the delivery device may be configured without such a coupler, so that the first plunger and the second plunger may be depressed independently of one another (e.g., sequentially).

The delivery device can further comprise a colorant (e.g., a dye). For example, the first syringe, the second syringe, or both the first syringe and the second syringe may comprise a colorant. The presence of a colorant facilitates the easy identification of the gas produced by the mixture of the acid and base, for example by producing a colored gaseous foam. This in turn facilitates the easy identification of any defects in the anatomical organ, which will be indicated by the presence of a colored gaseous foam escaping through such a defect.

A suitable colorant can be selected by those skilled in the art. Preferably, the colorant is a food grade coloring.

Acids and bases that are suitable for use in medical procedures are known to those skilled in the art. Non-limiting examples of suitable acids include $C_6H_8O_7$ (citric acid). Non-limiting examples of suitable bases include $NaHCO_3$ (sodium bicarbonate).

As used herein, the term "gaseous foam" refers to a mixture of a liquid and a gas wherein bubbles of the gas are dispersed on or in the liquid. Typically, the gaseous foam produced by the mixture of the acid and the base comprises carbon dioxide. The liquid component of the gaseous foam may comprise water, the acid, the base, and/or a colorant, among other components.

Typically, the delivery device comprises the acid and the base in a molar ratio of about 1:1. For example, the molar ratio of the acid to the base can be from about 1:10 to about 10:1, from about 1:5 to about 5:1, from about 1:4 to about 4:1, from about 1:3 to about 3:1, from about 1:2 to about 2:1, or about 1:1.

As a non-limiting, exemplary embodiment of a delivery device as described herein, FIG. 1 illustrates a delivery device 10 comprising a first syringe 14 and a second syringe 18.

The first syringe 14 includes a body 22 having a first end 26 and a second end 30. The body 22 is generally tubular (as illustrated) however the shape of the body may be square, elliptical, triangular, or other suitable shape. The first end 26 defines an opening 34 for receiving a plunger 38. The plunger 38 can include a seal. The first end 26 may include a flange partially or fully surrounding the opening 34. The second end 30 includes an outlet 42. The outlet 42 is generally defined by a reduced diameter portion 46.

The second syringe 18 is similarly constructed as the first syringe 14. The second syringe 18 includes a body 50 having a first end 54 and a second end 58. The body 50 is generally tubular (as illustrated) however the shape of the body may be square, elliptical, triangular, or other suitable shape. The first end 54 defines an opening 62 for receiving a plunger 66. The plunger 66 can include a seal. The top of plunger 66 can be connected (e.g., integral or with a separate connector) to the top of the plunger 38. The first end 54 may include a flange partially or fully surrounding the opening 62. The second end 58 includes an outlet 70. The outlet 70 is generally defined by a reduced diameter portion 74. In some constructions, the second syringe 18 is different than the first syringe 14. It is not a requirement that the first syringe 14 and the second syringe 18 be identical. The delivery device 10 may include a housing 76 that receives both the first syringe 14 and the second syringe 18 to align them relative to one another.

Figure 2:
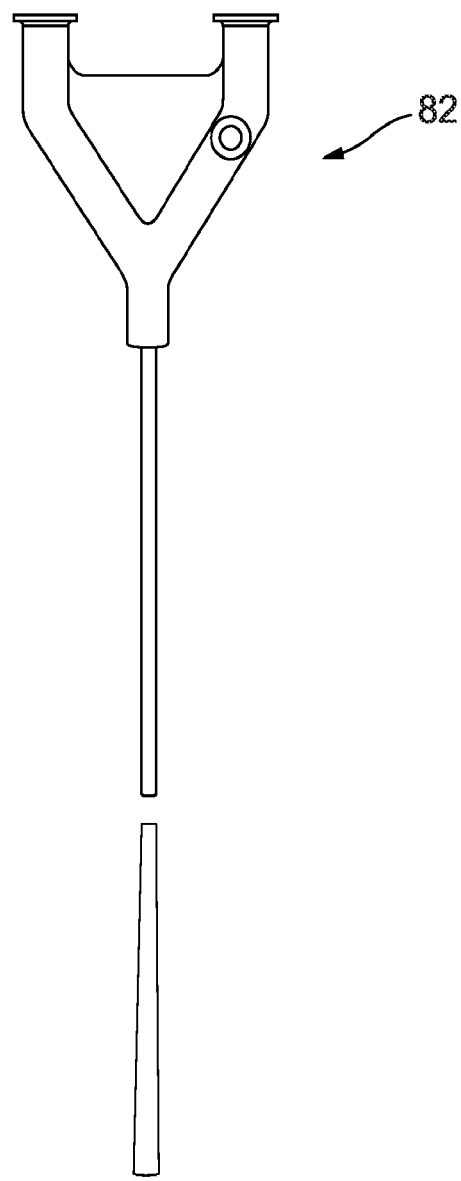
FIG. 2 illustrates Y-tubing for the delivery device illustrated in FIG. 1.

The first outlet 42 on the first syringe 14 is coupled to a first channel 78 of Y-tubing 82, and the second outlet 70 on the second syringe 18 is coupled to a second channel 86 of the Y-tubing 82. The first channel 78 has a first length and the second channel 86 has a second length. The first length and the second length are about the same and meet to form a third channel 94. The third channel 94 includes a dual lumen where the first channel 78 remains independent of the second channel 86. This configuration prevents the base and the acid from making contact until they exit from the third channel 94. The third channel 94 is sufficiently elongated with a small diameter or width such that it can fit into the anastomosis to inject a mixture (discussed below). An alternate construction of the Y-tubing 82 having a dual lumen is illustrated in FIG. 2.

In another construction, the first outlet 42 on the first syringe 14 is coupled to a first channel 78 of Y-tubing 82, and the second outlet 70 on the second syringe 18 is coupled to a second channel 86 of the Y-tubing 82. The first channel 78 has a first length and the second channel 86 has a second length. The first length and the second length are about the same such that an area 90 is defined at the junction where the first channel 78 and the second channel 86 meet to form a third channel 94. The third channel 94 is sufficiently elongated with a small diameter or width such that it can fit into the anastomosis to inject a mixture.

In a further construction, in lieu of the Y-tubing 82, the first outlet 42 is coupled to a first elongated tube, and the second outlet 70 is coupled to a second elongated tube. The first tube and the second tube are sufficiently elongated to fit into the anastomosis to inject a first component and a second component, described below.

The delivery device 10 includes two components. An acid and a base (e.g., a carbonate containing a base) that when combined yields a salt, $H_2O$, and $CO_2$. Any suitable acid and base may be utilized which results in production of a sufficient amount of $CO_2$ to distend a tissue. In an embodiment, the first component 98 comprises 7.5 grams of $C_6H_8O_7$ (citric acid) diluted in 5 ml of sterile water. In another embodiment, the first component 98 comprises 7.0 grams of citric acid diluted in 5-7 ml of sterile water or saline. In other constructions, the first component 98 can comprise 3-10 grams of citric acid in 3-10 ml of sterile water. The second component 102 comprises 7.5 grams of $NaHCO_3$ (baking soda) diluted in 5 ml of sterile water. In another embodiment, the second component 102 comprises 7.0 grams of citric acid diluted in 5-7 ml of sterile water or saline. In other constructions, the second component 102 can comprise 3-10 grams of baking soda in 3-10 ml of sterile water. A food grade coloring (e.g., about 5 drops) is optionally added (but not required) to either the first component 98 or the second component 102. When the first component 98 and the second component 102 are mixed, the mixture produces $CO_2$ and allows for distension of the segment of bowel with a foam or colored foam if the food grade coloring is used. The end products of the reaction are water/$CO_2$ and food coloring, if used, which are absorbed or excreted through the small intestine and or colon.

The first syringe 14 can be pre-loaded with the first component 98, and the second syringe 18 can be pre-loaded with the second component 102. In other constructions, a kit 106 may comprise the delivery device 10, a first container of the first component 98 and a second container of the second component 102. The optional food grade coloring may be in a separate container or included in the first container or the second container. The user may need to assemble the syringes 14, 18 by applying the plungers 38, 66 into the bodies 22, 50 and inserting the syringes 14, 18 into the housing 76. The user would fill the first syringe 14 with the first component 98 and fill the second syringe 18 with the second component 102 according to instructions that come with the kit 106. The optional food grade coloring can be added to the first syringe 14 or the second syringe 18 if it comes in a separate container. The user would connect the Y-tubing 82 to the outlets 42, 70 to ready the delivery device 10 for use.

Figure 3:
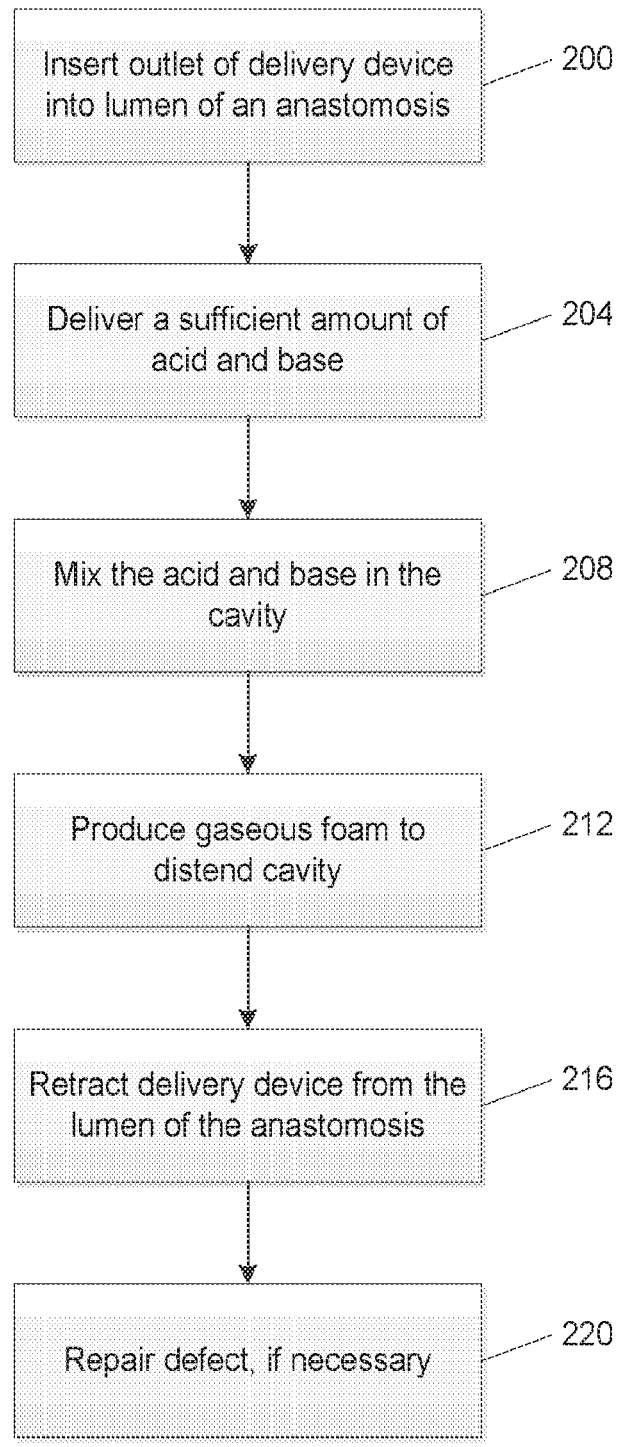
FIG. 3 illustrates a flow chart of a method of detecting leaks in an anastomosis according to an embodiment of the present invention.

In use and with reference to FIG. 3, bowel segments are anastomosed together in whichever fashion the operating surgeon chooses. For example, if a side-to-side anastomosis is performed there will be a common enterotomy. At the time of the closure of the common enterotomy (either stapled or hand sewn) the third channel 94 of the Y-tubing 82 of the delivery device 10 is placed (at step 200) in the lumen prior to closure. As force is applied to the plungers 38, 66, the first component and the second component travel through the outlets 42, 70 and into the first channel 78 and the second channel 86 (at step 204) that continue through the Y-tubing 82 into the cavity (at step 208) where the first component and the second component make contact. Alternatively, the third channel 94 may be relatively short with a mixing chamber that is positioned just outside the cavity such that the first component and the second component are mixed for as little time outside the cavity as possible. The mixture produces sodium citrate, water, and $CO_2$ with foam (colored foam if food grade coloring is used) (at step 212) in the cavity. The delivery device 10 is removed (at step 216) from the lumen in the anastomosis. The $CO_2$ causes the cavity to distend so atraumatic clamps are kept in place until the surgeon is satisfied that adequate distension has occurred to test for leaks. The clamps are removed and the $CO_2$ is absorbed into the blood stream and exhaled safely by the patient, with the sodium citrate excreted in the patient's stool. Should the surgeon feel the cavity is being too tightly distended the clamps can be removed. If the anastomosis is not air tight the $CO_2$/foam will leak out of the defect, showing exactly where the defect is located, and the surgeon can repair (at step 220) the leak in the anastomosis.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

In view of the above, it will be seen that the several objects of the disclosure are achieved and other advantageous results attained.

As various changes could be made in the above products and methods without departing from the scope of the disclosure, it is intended that all matter contained in the above description shall be interpreted as illustrative and not in a limiting sense.

Various features of the invention are set forth in the following claims.

What is claimed is:

1. A method for testing for leaks of an anastomosis of a bowel, the method comprising:
    inserting an outlet of a delivery device into a lumen of the anastomosis;
    delivering a sufficient amount of an acid and a sufficient amount of a base to the bowel;
    producing a gaseous foam when the acid and the base enter the bowel to distend the bowel;
    evaluating if there is a leak by the presence or absence of gaseous foam outside of the anastomosis; and
    retracting the outlet of the delivery device from the lumen of the anastomosis.

2. The method of claim 1, wherein the acid comprises from 1 to 20 grams of $C_6H_8O_7$ diluted in from 1 to 15 ml of sterile water.

3. The method of claim 1, wherein the base comprises from 1 to 20 grams of $NaHCO_3$ diluted in from 1 to 15 ml of sterile water.

4. The method of claim 1, wherein the molar ratio of the acid to the base is from about 1:5 to about 5:1.

5. The method of claim 1, further comprising repairing the anastomosis if the gaseous foam exits the anastomosis.

6. The method of claim 1 wherein the acid and the base are delivered into the cavity simultaneously.

7. The method of claim 1 wherein both the acid and the base are delivered into the cavity using a delivery device comprising:
    a first syringe comprising a base, the first syringe including a first body, a first plunger, and a first outlet;

a second syringe comprising an acid, the second syringe including a second body, a second plunger, and a second outlet; and tubing having a first channel coupled to the first outlet, a second channel coupled to the second outlet, and a third channel configured to be received in the lumen.

8. The method of claim 1 wherein both the acid and the base are delivered into the cavity using a delivery device comprising:

a first syringe comprising a base, the first syringe including a first body, a first plunger, and a first outlet;

a second syringe comprising an acid, the second syringe including a second body, a second plunger, and a second outlet;

a delivery tube extending from the first outlet and the second outlet and configured to deliver the acid and the base to the bowel.

9. A method for testing for leaks of an anastomosis of a bowel, the method comprising:

inserting an outlet of a delivery device into a lumen of the anastomosis;

delivering a sufficient amount of an acid and a sufficient amount of a base to the bowel;

producing a gaseous foam when the acid and the base enter the bowel to distend the bowel;

identifying if there is a defect in the anastomosis by the presence or absence of gaseous foam outside of the anastomosis; and retracting the outlet of the delivery device from the lumen of the anastomosis.

10. The method of claim 9, wherein the acid comprises from 1 to 20 grams of $C_6H_8O_7$ diluted in from 1 to 15 ml of sterile water.

11. The method of claim 9, wherein the base comprises from 1 to 20 grams of $NaHCO_3$ diluted in from 1 to 15 ml of sterile water.

12. The method of claim 9, wherein the molar ratio of the acid to the base is from about 1:5 to about 5:1.

13. The method of claim 9, further comprising repairing the anastomosis if the gaseous foam exits the anastomosis.

14. The method of claim 9 wherein the acid and the base are delivered into the cavity simultaneously.

* * * * *